(12) United States Patent
Su et al.

(10) Patent No.: US 11,215,563 B2
(45) Date of Patent: Jan. 4, 2022

(54) PHOTONIC APPARATUS, METHODS, AND APPLICATIONS

(71) Applicant: Arizona Board of Regents on Behalf of the University of Arizona, Tucson, AZ (US)

(72) Inventors: Tsu-Te Judith Su, Tucson, AZ (US); Euan McLeod, Tucson, AZ (US)

(73) Assignee: Arizona Board of Regents on Behalf of the University of Arizona, Tucson, AZ (US)

(*) Notice: Subject to any disclaimer, the term of this patent is extended or adjusted under 35 U.S.C. 154(b) by 0 days.

(21) Appl. No.: 16/310,685

(22) PCT Filed: Jun. 9, 2017

(86) PCT No.: PCT/US2017/036723
§ 371 (c)(1),
(2) Date: Dec. 17, 2018

(87) PCT Pub. No.: WO2018/005044
PCT Pub. Date: Jan. 4, 2018

(65) Prior Publication Data
US 2019/0178805 A1    Jun. 13, 2019

Related U.S. Application Data

(60) Provisional application No. 62/356,240, filed on Jun. 29, 2016.

(51) Int. Cl.
*G02B 6/12* (2006.01)
*G01N 21/77* (2006.01)
(Continued)

(52) U.S. Cl.
CPC ....... *G01N 21/7746* (2013.01); *G01N 21/554* (2013.01); *G02B 6/1226* (2013.01);
(Continued)

(58) Field of Classification Search
CPC .... G02B 5/008; G02B 5/1809; G02B 6/1226; G02B 2207/101; B82Y 20/10; G01N 21/554
(Continued)

(56) References Cited

U.S. PATENT DOCUMENTS 4,829,537 A * 5/1989 Baer ..................... G01C 19/64
356/459
6,633,696 B1 * 10/2003 Vahala .................. B82Y 20/00
385/1

(Continued)

FOREIGN PATENT DOCUMENTS

GB       2517955       6/2016

OTHER PUBLICATIONS

"The curvature and geodesics of the torus" by Irons, 2005.*
(Continued)

*Primary Examiner* — Robert Tavlykaev
(74) *Attorney, Agent, or Firm* — Venable LLP; Henry J. Daley

(57) ABSTRACT

An optical microtoroid resonator including one or more nanoparticles attached to a surface of the resonator and capable of receiving an input signal from a far-field source (via free-space transmission) and outputting light propagating within the optical apparatus. A method for coupling light into and out of an optical resonator using a nanoparticle or nanoparticles to interface with spatially separated far-field optical elements.

12 Claims, 5 Drawing Sheets

(51) Int. Cl.
  *G02B 6/122* (2006.01)
  *G01N 21/552* (2014.01)
  *B82Y 20/00* (2011.01)
  *G01N 33/543* (2006.01)

(52) U.S. Cl.
  CPC ........ *B82Y 20/00* (2013.01); *G01N 33/54373* (2013.01); *G01N 2021/7789* (2013.01)

(58) Field of Classification Search
  USPC .............................................. 385/31, 32, 35
  See application file for complete search history.

(56) References Cited

U.S. PATENT DOCUMENTS

| | | | | |
|---|---|---|---|---|
| 6,928,091 | B1* | 8/2005 | Maleki | H03B 21/02 |
| | | | | 359/237 |
| 7,693,369 | B2* | 4/2010 | Fan | G01N 21/7746 |
| | | | | 385/2 |
| 7,903,240 | B2* | 3/2011 | Smith | G01N 21/7746 |
| | | | | 356/39 |
| 7,941,015 | B2* | 5/2011 | Bratkovski | B82Y 20/00 |
| | | | | 385/30 |
| 8,107,081 | B2* | 1/2012 | Armani | G01N 21/783 |
| | | | | 356/437 |
| 8,178,202 | B2 | 5/2012 | Halas et al. | |
| 9,507,178 | B1* | 11/2016 | Blackledge | G02F 1/011 |
| 9,709,476 | B2* | 7/2017 | Arnold | G01N 15/0205 |
| 2007/0269901 | A1* | 11/2007 | Armani | G02B 6/29343 |
| | | | | 436/172 |
| 2008/0094621 | A1* | 4/2008 | Li | G01J 3/44 |
| | | | | 356/301 |
| 2009/0310902 | A1* | 12/2009 | Smith | G01N 21/7746 |
| | | | | 385/12 |
| 2011/0139970 | A1* | 6/2011 | He | G01N 21/7746 |
| | | | | 250/227.18 |
| 2011/0150485 | A1* | 6/2011 | Seidel | H03D 9/00 |
| | | | | 398/115 |
| 2012/0069331 | A1 | 3/2012 | Shopova et al. | |
| 2012/0113419 | A1* | 5/2012 | Wang | B82Y 15/00 |
| | | | | 356/301 |
| 2012/0194893 | A1* | 8/2012 | Maleki | G02F 2/02 |
| | | | | 359/246 |
| 2012/0281957 | A1* | 11/2012 | Chamanzar | B82Y 20/00 |
| | | | | 385/131 |
| 2012/0309080 | A1* | 12/2012 | Cunningham | G01N 21/658 |
| | | | | 435/288.7 |
| 2013/0286467 | A1 | 10/2013 | Vlasko-Vlasov et al. | |
| 2015/0301034 | A1 | 10/2015 | Su | |
| 2016/0195676 | A1* | 7/2016 | Yu | G02B 6/107 |
| | | | | 385/11 |
| 2017/0025813 | A1* | 1/2017 | Eden | H01S 3/10092 |
| 2020/0142277 | A1* | 5/2020 | Ebrahim-Zadeh | G02F 1/39 |

OTHER PUBLICATIONS

Notification of Transmittal, International Search Report, and Written Opinion dated Oct. 6, 2017, for PCT Application PCT/US2017/036723; 10 pages.
Su, J., et al., Label-free detection of single nanoparticles and biological molecules using microtoroid optical resonators, Light: Science & Applications 5, e16001, doi:10.1038/lsa.2016.1, pp. 1-6 (2016).
Vahala, K. J., Optical microcavities, Nature vol. 424, pp. 839-846, copyright 2003 Nature Publishing Group.
Armani, D. K., et al., Ultra-high-Q toroid microcavity on a chip, Nature vol. 421, pp. 925-928, doi:10.1038/nature01371, copyright 2003 Nature Publishing Group.
Baaske, Martin. D., et al., Single-molecule nucleic acid interactions monitored on a label-free microcavity biosensor platform, Nature Nanotechnology vol. 9, pp. 933-939, doi:10.1038/nnano.2014.180, copyright 2014 Macmillan Publishers Limited.
Vollmer, F., et al., Single virus detection from the reactive shift of a whispering-gallery mode, Proc. Natl. Acad. Sci. U. S. A., vol. 105, No. 52, pp. 20701-20704, doi:10.1073/pnas.0808988106 (2008).
Dantham, Venkata R., Label-Free Detection of Single Protein Using a Nanoplasmonic-Photonic Hybrid Microcavity, Nano Letters, 13, pp. 3347-3351, doi:10.1021/nl401633y, copyright 2013 American Chemical Society.
Su, Judith, Label-Free Single Exosome Detection Using Frequency-Locked Microtoroid Optical Resonators, ACS Photonics 2, pp. 1241-1245, doi:10.1021/acsphotonics.5b00142, copyright 2015 American Chemical Society.
Hansen, Poul Martin, et al., Expanding the Optical Trapping Range of Gold Nanoparticles, Nano Letters vol. 5, No. 10, pp. 1937-1942, doi:10.1021/nl051289r, copyright 2005 American Chemical Society.
Harada, Yasuhiro, et al., Radiation forces on a dielectric sphere in the Rayleigh scattering regime, Optics Communications, 124, pp. 529-541, doi:http://dx.doi.org/10.1016/0030-4018(95)00753-9, copyright 1996 Elsevier Science B.V.
Rakić, Aleksandar D., et al., Optical properties of metallic films for vertical-cavity optoelectronic devices, Applied Optics vol. 37, No. 22, pp. 5271-5283, doi:10.1364/AO.37.005271, copyright 1998 Optical Society of America.
McLeod, Euan, et al., Array-based optical nanolithography using optically trapped microlenses, Optics Express vol. 17, No. 5, pp. 3640-3650, doi:10.1364/OE.17.003640, copyright 2009 Optical Society of America.
Li, Shi-Qiang, et al., Ultra-sharp plasmonic resonances from monopole optical nanoantenna phased arrays, Applied Physics Letters 104, pp. 231101-1-231101-5, doi:doi:http://dx.doi.org/10.1063/1.4881323, copyright 2014 AIP Publishing LLC.
Arango, Felipe Bernal, et al., Robustness of plasmon phased array nanoantennas to disorder, Scientific Reports 5, 10911, doi:10.1038/srep10911, pp. 1-9, (2015).
Cecchini, Michael P., et al., Self-assembled nanoparticle arrays for multiphase trace analyte detection, Nature Materials vol. 12, pp. 165-171, doi:http://www.nature.com/nmat/journal/v12/n2/abs/nmat3488.html#supplementary-information, copyright 2013 Macmillan Publishers Limited.
Suh, Jae Yong, et al., Plasmonic Bowtie Nanolaser Arrays, Nano Letters 12, pp. 5769-5774, doi:10.1021/nl303086r, copyright 2012 American Chemical Society.
Kleinhenz, Matthew D., et al., Using 0Brix as an Indicator of Vegetable Quality: Instructions for Measuring 0Brix in Cucumber, Leafy Greens, Sweet Corn, Tomato and Watermelon, copyright 2015 The Ohio State University, 13 pages.
Stoller-Conrad, Jessica, SKIES App Aids Learning in Caltech Classrooms, Dec. 17, 2014, https://www.caltech.edu/news/skies-app-aids-learning-caltech-classrooms-45106, 3 pages.
Zhang, Yongxia, et al., Metal Enhanced Fluorescence, Edited by Chris D. Geddes, Metal Enhanced Chemiluminescence, John Wiley & Sons, Inc., 2010, pp. 439-463.
NanoComposix, Inc., 50 nm Gold Nanospheres, PEG Carboxyl, Ultra Uniform (Lot No. DMW0867A); https://tools.nanocomposix.com:48/cdn/coa/Gold/Spheres/Ultra%20Uniform/Au50_UU_PEG-COOH_0.05mg_mL_DMW08867A_CoA.pdf: printed Dec. 11, 2019.
Novotny, Lukas et al., Principles of Nano-Optics, second edition, Cambridge University Press 2012, Chapters 2 (pp. 12-44), 3 (pp. 45-85), 8 (pp. 224-281), 11 (pp. 338-368), 12 (pp. 369-413), 13 (pp. 414-447) and 14 (pp. 448-473).

* cited by examiner

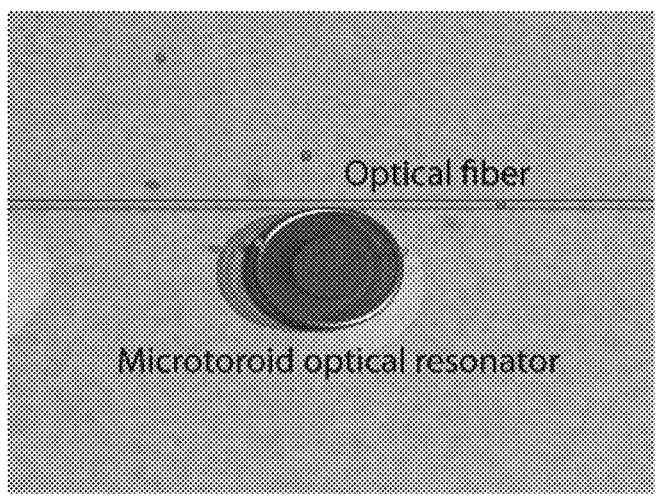
FIG. 1
(Prior art)
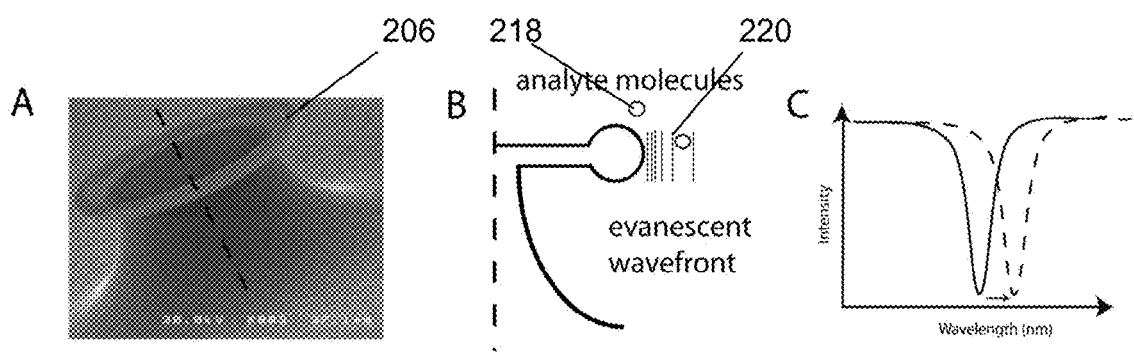
| Microtoroid scanning electron micrograph | Microtoroid cross-section | Molecular binding is detected by shifts in the resonance frequency |
| Fig. 2A | Fig. 2B | Fig. 2C |
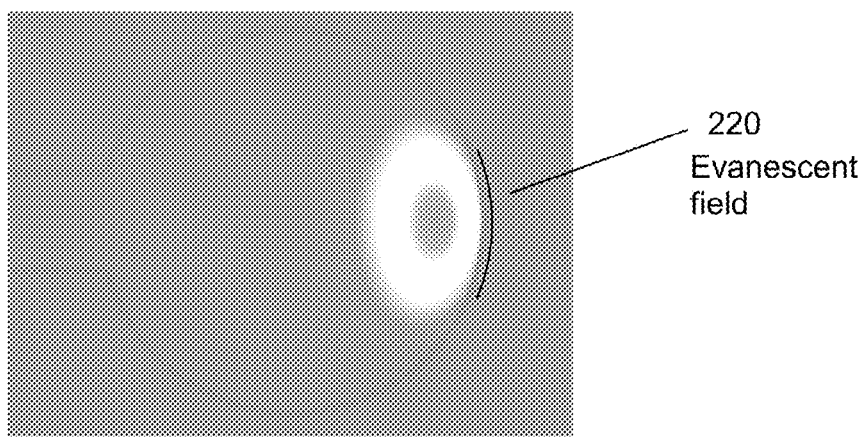
FIG. 3

Cartoon (not to scale) of a phased array / metasurface fabricated on a toroid

PHOTONIC APPARATUS, METHODS, AND APPLICATIONS

RELATED APPLICATION DATA

This application is a U.S. National Phase filing of International Application Number PCT/US2017/036723 filed Jun. 9, 2017, which relates and claims priority to U.S. Provisional Application No. 62/356,240 filed Jun. 29, 2016, the subject matter of each of which is hereby incorporated by reference in their entirety.

GOVERNMENT FUNDING

N/A.

BACKGROUND

Aspects and embodiments of the invention are in the field of photonics; more particularly, photonic apparatus, methods, and applications; most particularly, photonic resonator apparatus incorporating nanoparticles, associated methods, and applications thereof.

Sensitive and portable sensors are desirable for a wide variety of applications including early disease diagnosis and prognosis, monitoring food and water quality, as well as detecting bacteria and viruses for public health concerns. Frequency-locked microtoroid optical resonators have been shown to be extremely sensitive sensors capable of detecting individual protein molecules at a concentration of one part in a quadrillion (0.001 pg/mL).

It would be beneficial and advantageous to miniaturize these sensors in order to make them portable and easily translatable to other laboratories or the field. Currently, however, light is coupled into these sensors using a tapered optical fiber (FIG. 1) that is lifted off of the substrate, requiring alignment with nanoscale precision relative to the microtoroid resonator. The time-consuming fabrication and alignment of this tapered optical fiber is one of the main impediments to easy miniaturization and scalable manufacturing of microtoroid optical resonator sensing systems.

It would thus be further beneficial and advantageous to have a photonic resonator apparatus that does not require an external waveguide (e.g., tapered optical fiber) to couple light into and out of the resonator, as well as methods and techniques to more easily manufacture such apparatus having increased detection sensitivity, in larger quantities. A further increase in sensitivity of these sensors would be useful for detecting even smaller signals such as those that would be generated from smaller molecules than have been previously detected, or for detecting conformational changes within a single protein.

SUMMARY AND NON-LIMITING DISCUSSION

An aspect of the invention is an optical apparatus capable of receiving an input signal from a far-field source (via free-space transmission) and outputting light propagating within the optical apparatus. According to an exemplary embodiment, the apparatus consists of an optical resonator including one or more nanoparticles attached to a surface of the resonator. According to various exemplary, non-limiting embodiments, the apparatus may additionally include one or more of the following components, assemblies, features, limitations or characteristics, alone or in various combinations as one skilled in the art would understand:

wherein the one or more nanoparticles are plasmonic nanoparticles;
wherein the one or more nanoparticles is a high refractive index dielectric or semiconductor;
wherein the one or more nanoparticles is at least one of Si, Ge, Te, GaAs;
characterized in that the optical apparatus operates as a label-free biosensor;
characterized in that the optical apparatus operates as a single molecule detector;
wherein the one or more nanoparticles are non-spherical;
wherein the one or more non-spherical nanoparticles have a polarization that is aligned with a polarization of a light in the optical resonator;
wherein the one or more non-spherical nanoparticles have a bow-tie geometry;
wherein the one or more nanoparticles are at least one of a nanoshell, a gold nanosphere, a silver nanosphere, a nanorod, a nanoplate, and a metal-dielectric composite nanoshell;
wherein the optical resonator is characterized by a quality factor, Q, that is equal to or greater than $10^5$;
wherein the optical resonator is a silica microtoroid;
wherein the one or more nanoparticles are chemically attached to the microtoroid;
wherein the one or more nanoparticles comprise a phased array of nanoparticles;
wherein the one or more nanoparticles comprises a metasurface;
wherein the one or more nanoparticles comprise one or more groupings of nanoparticles;
wherein assemblies of nanoparticles are used.

An aspect of the invention is a method for coupling light into and out of an optical resonator using a nanoparticle or nanoparticles to interface with spatially separated far-field optical elements. According to various exemplary, non-limiting embodiments, the method may additionally include one or more of the following steps, components, assemblies, features, limitations or characteristics, alone or in various combinations as one skilled in the art would understand:

further comprising non-randomly attaching a nanoparticle to an optical resonator comprising positioning and attaching a nanoparticle to a desired location within +0.5-100 nm along a surface of the resonator, wherein a hotspot of ultra-high electric field intensity ($E_w$/nano=10 to 1000× $E_w$/o nano) is created within an evanescent zone of the resonator;
further comprising using one of an optical tweezer and an atomic force microscope technique/apparatus or micronozzle to position and attach the nanoparticle to the desired location;
wherein the nanoparticle is a plasmonic nanoparticle;
wherein the nanoparticle is a high refractive index dielectric or semiconductor;
wherein the nanoparticle is at least one of Si, Ge, Te, GaAs;
wherein the desired location is an equatorial (circumferential) region of a microtoroid;
wherein the optical resonator is an optical micro-resonator;
further comprising positioning and attaching a maximum plurality of nanoparticles to a respective plurality of desired locations (+0.5-100 nm) along the surface of the resonator;
wherein the one or more nanoparticles are non-spherical, further comprising controlling the orientation of the non-spherical nanoparticle so as to align the particle's direction of maximum polarizability with the polarization of a light in the optical resonator;

wherein the desired location is a known position that provides an operational interface, which enables input/output of light to/from the resonator via an external element;

further comprising positioning and attaching at least one of a nanoshell, a gold nanosphere, a silver nanosphere, a nanorod, a nanoplate, and a metal-dielectric composite nanoshell;

further comprising using the optical resonator to detect a single molecule of an analyte;

further comprising using the optical resonator to detect a single protein molecule;

comprising chemically attaching the nanoparticle to the resonator;

further comprising coating the nanoparticle with streptavidin; and covalently binding a silane-PEG-biotin linker to the resonator surface;

further comprising attaching the nanoparticle to the resonator via at least one of covalent bonding; chemisorption; and noncovalent interactions.

BRIEF DESCRIPTION OF THE DRAWINGS

FIG. 1: Schematic top perspective view showing how light is coupled into a microtoroid optical resonator from an optical fiber, as known in the art.

FIG. 2: A microtoroid is an example of a whispering gallery mode optical resonator. FIG. 2A) A scanning electron micrograph of a microtoroid; FIG. 2B) A schematic of the evanescent wavefront interacting with molecules near the microtoroid (not to scale); FIG. 2C) Graphical representation showing that molecules binding to the toroid's surface change the resonant frequency of the device, according to illustrative embodiments of the invention.

FIG. 3 is a finite element COMSOL simulation of the capacitive Poynting energy density inside a silica microtoroid with major and minor diameters of 90 and 4 microns, respectively. The view presented is of a cross-section of the microtoroid. The toroid is immersed in water. Part of the electric field evanesces beyond the rim of the microtoroid (solid line). This is the sensing region of our device and it is localized to the rim of the toroid, according to an illustrative embodiment.

DETAILED DESCRIPTION OF NON-LIMITING, EXEMPLARY EMBODIMENTS

We disclose herein, among other things, an ultra-sensitive and portable (self-contained), optical resonator-based sensor and the nano-manufacturing of an ultra-sensitive and portable (self-contained), optical resonator-based sensor having one or more nanoparticles disposed on the surface of the optical resonator with precise positioning (to within ±0.5-100 nm depending on nanoparticle dimensions).

Metal (plasmonic) nanostructures have been shown to generate locally enhanced electric fields due to surface plasmon excitation when illuminated with light from the far-field. According to an aspect, we precisely position and fix one or more plasmonic nanostructures in targeted locations on the surface of a microtoroid optical resonator. This may be accomplished using optical tweezers. Thereafter, we observe "hotspots" of ultra-high electric field intensities ($E_{w/nano}$=10× to 1000× $E_{w/o\ nano}$) created within the evanescent zone of the microtoroid as illustrated in FIG. 3.

Other photonic resonator geometries may be used such as microspheres, bubbles, linear Fabry-Perot, bottles, droplets, cylindrical capillaries, disks, and rings, as well as alternative positioning and attachment methodologies including but not limited to atomic force microscopy and micronozzle deposition as are known in the art.

Figure 4:
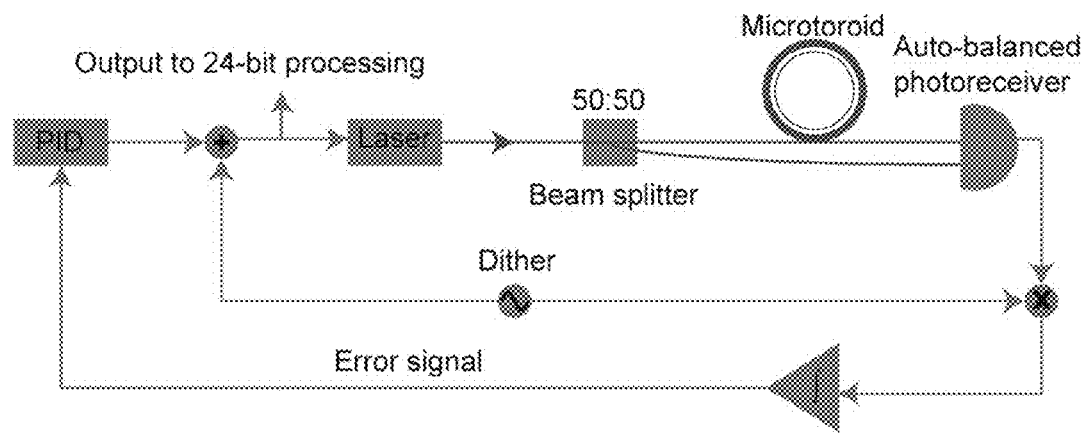
FIG. 4: Block diagram of FLOWER. A small, high-frequency dither is used to modulate the driving laser frequency.

We previously developed a biosensing technique known as FLOWER (frequency locked optical evanescent resonator; US 2015/0301034) that uses frequency-locked microtoroid optical resonators to detect single unlabeled macromolecules. FLOWER has been shown capable of detecting unlabeled single human-interleukin-2 molecules that have a mass of 0.002 attograms. In addition to being more sensitive, FLOWER eliminates the need to label the target molecule, thus providing a reduction in the complexity and cost when compared to other assays such as an enzyme-linked immunosorbent assay (ELISA). As illustrated in FIG. 4, the dither signal, when multiplied by the toroid output and time-averaged generates an error signal whose amplitude is proportional to the difference between the current laser frequency and resonant frequency. This error signal is sent to a PID controller, whose output is used to set the laser frequency, thus completing the feedback loop. A computer records the observed frequency shifts.

Figure 13:
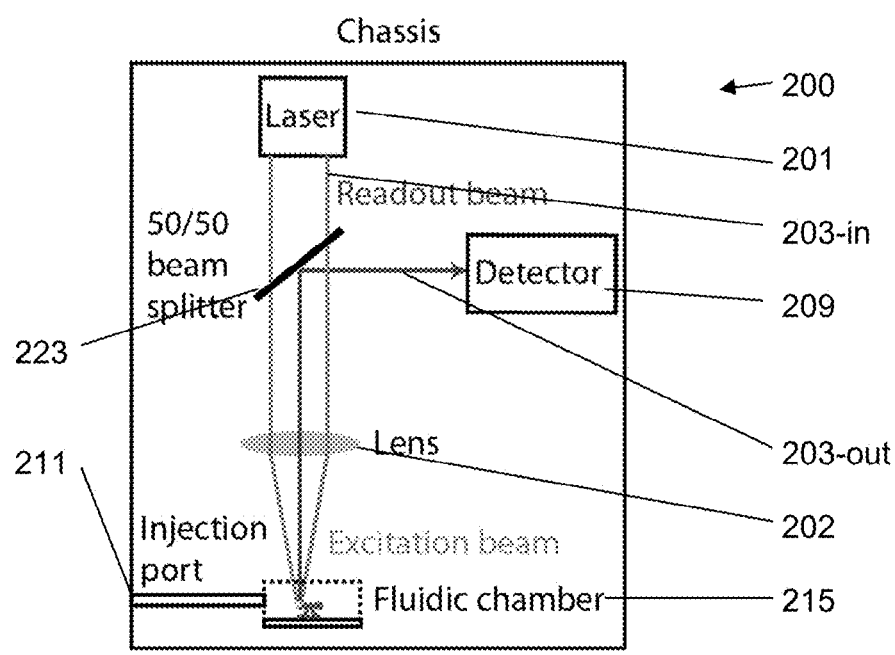
FIG. 13 schematically illustrates a portable FLOWER apparatus, according to an illustrative embodiment of the invention.

An exemplary embodiment of the invention is a miniaturized FLOWER apparatus 200 that is part of a self-contained, compact, portable device, which is able, for example, to be used in the field to quickly diagnose and establish the prognosis of various diseases. FIG. 13 schematically illustrates a portable FLOWER apparatus 200, according to an illustrative embodiment of the invention. Light $203_{in}$ is focused from the far-field (laser 201) by a lens 202 onto a nano-antenna 205 that has been positioned on the surface of a microtoroid 206. The back-scattered light $203_{out}$ from the antenna is sent to a balanced detector 209. An injection port 211 is located on the side of the chassis to enable sample delivery into fluidic chamber 215. In the inventive embodiments, the optical fiber used to evanescently couple light into and out the device is replaced with a more compact and robust solution, resulting in a device with higher sensitivity and capable of detecting smaller molecules such as insulin, or smaller signal changes that arise as a protein changes conformation. We incorporate nanomaterials, advantageously plasmonic nanoparticles, into the system to make it more readily manufacturable. The nanoparticles may include nanoshells, gold nanospheres, silver nanospheres, nanorods, nanoplates, nano-bowties, and metal-dielectric composite nanoshells.

While past work has reported the use of gold nanoshells and nanorods with microsphere resonators to create sensing hotspots, these particles have been positioned randomly. Furthermore, they have only been used as sensing hot spots, and not as a means to effectively couple light into and out of the devices. The random positioning is also non-ideal for sensing purposes because the effectiveness of a plasmonic hot spot depends sensitively on which part of the optical resonator the plasmonic particle is located; the ideal location is at the equatorial region where the evanescent field is greatest (see FIG. 3). Thus, a randomly-positioned particle is likely to generate observed detection signals that are lower in amplitude and higher in noise than for optimally positioned particles as embodied herein.

In the embodied invention, instead of the random placement that has been used previously, we propose precise, predetermined placement of these structures through nano-manufacturing, maximizing the number of these structures that can be placed on our sensor as well as optimizing their positioning, thereby maximizing our effective sensor capture area. In addition, the embodied approach allows us to control the orientation of these structures, which allows us to align their direction of maximum polarizability with the polarization of the light orbiting in the optical resonator, in the case where the nanostructures are nonspherical. This alignment maximizes the electric field enhancement provided by the nanostructures. Finally, we can localize nanostructures at known positions on the resonator surface to interface with far-field micro-optical elements to launch light into the resonator, as well as to read out a signal, side-stepping the cumbersome nature of coupling to the resonator with a tapered optical fiber (FIG. 1) as known in the art.

A microtoroid optical resonator 206 as shown in FIG. 2A can function as an extremely sensitive sensor. More particularly, it may function as label-free sensor that can detect the presence of particles or molecules by measuring small refractive index changes without the need for fluorescent or radioactive tagging of the target of interest.

Microtoroid optical resonators operate on the principle of resonant recirculation of light. They are the optical analog of an acoustic whispering gallery, first described by Lord Rayleigh. He reportedly stood under the dome of St. Paul's Cathedral in London and noticed that whispers at one end of the dome could be heard 40 meters away at the other end of the dome as sound skirts along the edges with negligible loss. Optical resonators operate under the same physical principle based on light instead of sound.

Light is evanescently coupled into these devices (as known) and is continuously totally internally reflected within them, generating an evanescent field 220 as illustrated in FIG. 2B and by the solid curved line 220 in FIG. 3. When a particle 218 having a different refractive index (or polarizability) than the background medium enters the evanescent field 220, part of the light enters the particle, changing the optical path length of the light and decreasing the frequency at which the toroid resonates. This enables sensitive monitoring of particle binding events as illustrated in FIG. 2C. Because light circulates multiple times within the device before exiting, it interacts multiple times with a particle, making the microtoroid a more sensitive sensor than a traditional single-pass device such as a waveguide or cuvette. More traditional optical resonators such as microrings have demonstrated picomolar sensitivities of proteins but have not been able to detect single molecules. Microspheres have reportedly been shown capable of detecting single Influenza A virus particles but not single protein molecules. Recently, researchers have adhered gold nanoshells and nanorods to the surface of microspheres to create small plasmonic-enhanced sensing hotspots for detecting proteins and DNA. A microtoroid geometry appears to be the most advantageous choice to optimize sensitivity to the smallest possible particles.

Figure 5:
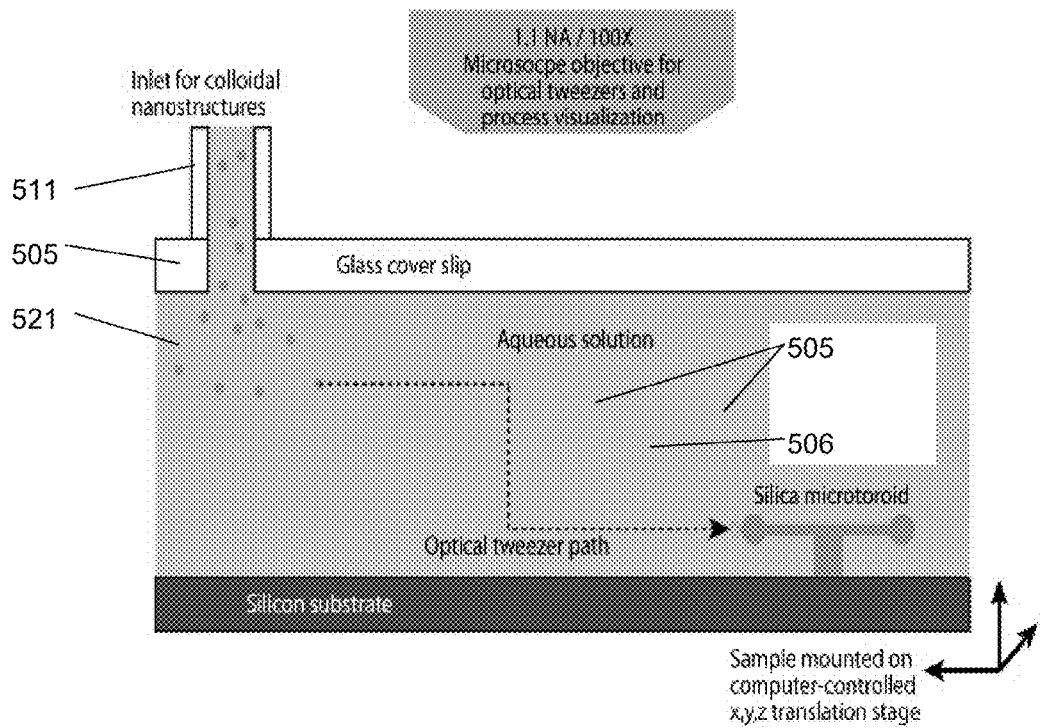
FIG. 5 schematically illustrates a nanostructure positioning process based on optical tweezers to position individual nanostructures at the rim of a silica microtoroid, which has been previously fabricated on a silicon wafer, according to an illustrative embodiment of the invention.
Figure 6:
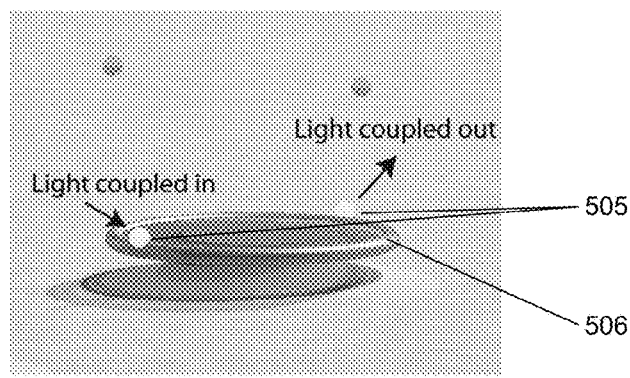
FIG. 6: Artistic rendering showing how light will be coupled into and out of a microtoroid optical resonator using gold nanoshells (white dots), according to an illustrative embodiment of the invention. The darker particles are unbound particles of interest.

According to an embodied method, we use optical tweezers to precisely position nanostructures (e.g., gold spherical and bowtie-shaped) on the sensing region (rim) of a silica microtoroid which has been previously fabricated on a silicon wafer as illustrated in FIG. 5. A microfluidic chamber 500 was constructed around the microtoroid 506 with an inlet 511 and an outlet (not shown), each located far away (on the order of millimeters) from the microtoroid. Nanostructures 505 were suspended in a fluid 521 and introduced into the microfluidic chamber through, e.g., a manual syringe, syringe pump, microfluidic flow controller, or capillary action (not shown). The inlet was located far enough away from the microtoroid such that it is statistically improbable for nanoparticles that enter the microfluidic channel to encounter the microtoroid via diffusion alone. Chemical interactions (described herein below) fix the nanostructures in place on the microtoroid, as further illustrated in FIG. 6. When illuminated with light, these structures have demonstrated enhanced electric fields, $E_w$, of up to 1000× in the case of a nanobowtie.

Figure 11:
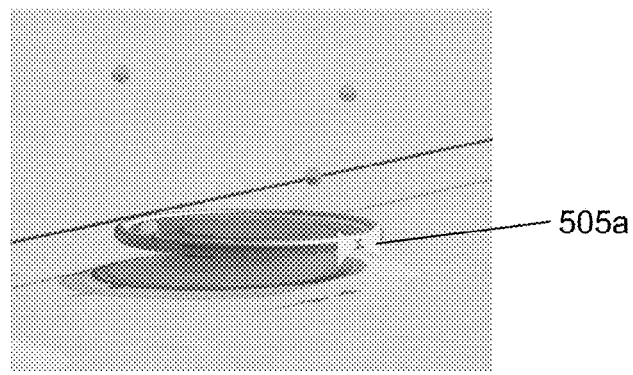
FIG. 11: Artistic rendering of a gold nanobowtie (not to scale) bound to the surface of a microtoroid, according to an illustrative embodiment of the invention.

Out of a wide range of potential plasmonic materials, such as gold nanospheres, silver nanospheres, nanorods, nanoplates, nanobowties, or metal-dielectric composite nanoshells, we initially used simple spherical gold nanospheres with a diameter of 50 nm. Although the plasmon resonance of these particles (peak at λ=528 nm) did not precisely match the operating range of our current tunable laser system (632.5 nm<λ<637 nm), the plasmon resonance of the particles is broad and some of the plasmon resonance tail extends into the wavelength range of the laser system, making coupling feasible. Even when the nanoparticle is not resonant at the excitation wavelength, non-resonant oscillations will still occur and which can be used to couple light into the microtoroid as well as amplify biosensing. Simple gold nanospheres of this size can be optically trapped using a conventional high-NA focused-beam optical tweezer. It is likely that many of the other types of nanomaterials may also be feasibly trapped; however nonspherical particles have non-isotropic polarizabilities that can complicate and potentially disrupt the optical trap. We explore some of these more exotic nanoparticle shapes, in the form of pairs of triangular nano-plates aligned to form a nanobowtie 505a (FIG. 11).

As mentioned herein above, the nanospheres serve two purposes: (1) to couple light into and out of the microtoroid (FIG. 6) and eliminate the need for an optical fiber, and (2) to serve as a sensing hotspot for biological/chemical molecules. We performed finite element simulations, as described below, in order to determine the maximum number of gold nanospheres that we can place around the rim of the microtoroid while still maintaining quality (Q) factors of our device above $10^5$. Q is a measure of the energy storage capabilities of a resonator and is defined as $\Delta\lambda/\lambda$, where $\lambda$ is the center wavelength of the resonance peak and $\Delta\lambda$ is the full width of the peak at half of the maximum value. Excessive numbers of gold nanospheres can lead to excessive scattering loss, which will eventually degrade the Q of microtoroid. In this way the use of these plasmonic particles is a "two-edged sword;" i.e., efficient coupling enables the whispering gallery mode to be efficiently launched into the device and read out, while at the same time leads to scattering losses. On the other hand, the more nanospheres that can be precisely positioned around the rim of the toroid, the more sensing hotspots that are created. We also used simulation to investigate the effect of nanoparticle size on coupling efficiency and optimizing this balance.

Full-wave electromagnetic simulations of the microtoroidal resonator were performed using COMSOL and MEEP. MEEP is an open-source software package developed at the Massachusetts Institute of Technology (MIT). We modeled surface roughness, material absorption, and nonlinearities.

In parallel to designing the precise locations and optimum number of nanoparticles to adhere to the toroid, we developed techniques to precisely position and bind nanoparticles to highly curved silica structures like microtoroids. The embodied manufacturing methods incorporate various optical traps whose performance determines the maximum speed with which particles can be adhered to the microtoroids, which will limit the rate of manufacturing of such devices, as well as positioning accuracy, which limits the manufacturing precision tolerance.

Figure 7:
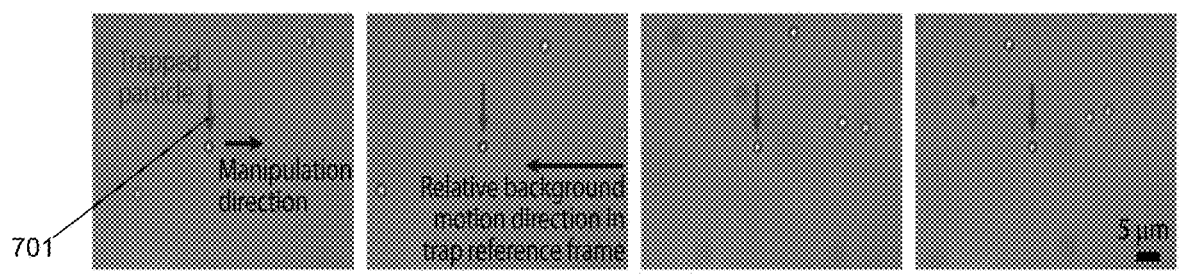
FIG. 7 shows four successive frames showing optical trapping and manipulation of a polystyrene bead relative to other beads undergoing Brownian motion in the background, according to an illustrative embodiment of the invention.

These manufacturing parameters were quantified using our available optical trapping system. The key elements of the system include: (1) a 30 W continuous-wave laser operating at $\lambda$=1064 nm wavelength with high power stability (<2% variation) and mode quality $M^2$<1.1; (2) a 100×/1.1 NA water immersion microscope objective corrected into the infrared with a cover glass correction collar; and (3) a nanopositioning stage with 1 nm resolution, total travel distance of 26 mm, <1 nm repeatability (over a reduced 100 μm travel distance), and maximum speed of 20 mm/s. FIG. 7 shows four successive frames showing optical trapping and manipulation of a polystyrene bead 701 relative to other beads undergoing Brownian motion in the background. A single bead is trapped in the center of the field of view. Here, the optical trap and microscope visualization are in a fixed reference frame, while the substrate and background beads exhibit the relative motion of a computer-controlled translation stage.

Figure 8:
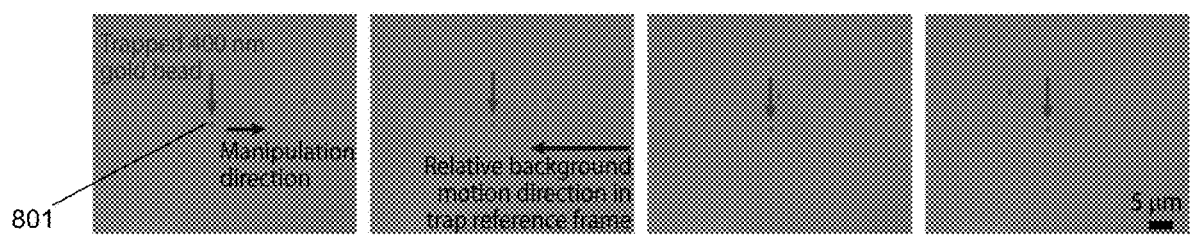
FIG. 8 shows four successive frames showing optical trapping and manipulation of a single 400 nm gold nanoparticle, according to an illustrative embodiment of the invention.

Beyond this simple demonstration of conventional optical trapping, we have also verified that we can trap metallic particles. FIG. 8 shows four successive frames showing optical trapping and manipulation of a single 400 nm gold nanoparticle 801. A single 400 nm gold particle is trapped in the center of the field of view. Four successive frames show this particle being manipulated relative to a freely-floating particle in the background. In this experiment, the optical trap and microscope visualization are in a fixed reference frame, while the substrate and background beads exhibit the relative motion of the computer-controlled translation stage.

While in general metals have very different optical properties from dielectrics, spherical nanoparticles of both materials can be optically trapped via the same mechanism as long as the particle size is significantly smaller than the wavelength of the trapping beam. In fact, because of the enhanced polarizability of metals relative to dielectrics, they are trapped more easily. The governing equation for optical trapping gradient force (lateral force) for particles significantly smaller than the wavelength (Rayleigh particles) is $$F_{grad} = \frac{\text{Re}\{\alpha\}}{2} \nabla \langle |E|^2 \rangle, \tag{1}$$

where $\langle |E|^2 \rangle$ is the time-averaged magnitude-squared of the electric field and $\alpha$ is the complex polarizability of the particle, given by the Clausius-Mossotti relation, $$\alpha = V \frac{\epsilon_p - \epsilon_w}{p\epsilon_p + 2\epsilon_w} 3\epsilon_0, \tag{2}$$

where $V_p$ is the particle volume, $\epsilon_p$ is the dielectric constant of the particle, $\epsilon_w$ is the dielectric constant of the surrounding water, and $\epsilon_0$ is the free-space permittivity. For a 50 nm diameter silica particle, $\text{Re}\{\alpha\} \approx 1.0 \times 10^{-34}$ $\text{Cm}^2\text{V}^{-1}$, while for the same size of gold particle $\text{Re}\{\alpha\} \approx 2.0 \times 10^{-33}$ $\text{Cm}^2\text{V}^{-1}$. This translates into the gold nanoparticle being approximately 20 times easer to trap than the silica nanoparticle, and both particles can be trapped at the focus of a tightly-focused laser beam.

In addition to gradient forces, another type of force called the scattering force is important in trapping particles in the z-direction. As a result, the trap in the z-direction tends to be weaker than in the transverse directions, however we do not expect this to significantly impact our approach because the time-limiting step from a manufacturing point of view will be the time it takes to drag a particle transversely toward the optical resonator.

Figure 9:
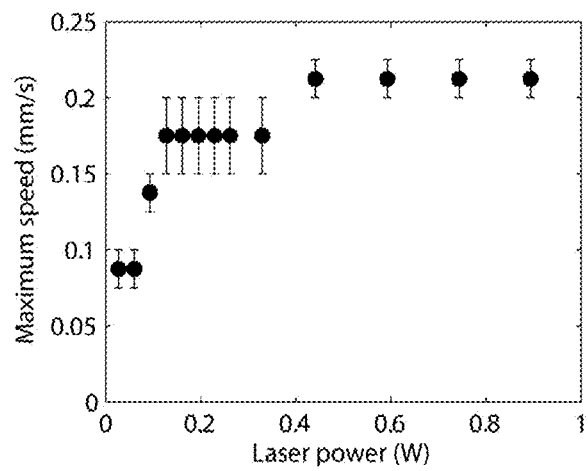
FIG. 9 graphically illustrates experimentally-measured maximum manipulation speeds of 1 μm-diameter polystyrene particles, according to an illustrative embodiment of the invention. The experimentally-measured maximum manipulation speeds of 1 μm-diameter polystyrene particles are plotted.

The strength of the optical trapping force directly affects the maximum particle manipulation speed. The maximum manipulation speed is important as it can limit the speed with which nanostructures can be brought to the microtoroid. Before measuring manipulation speeds for nano-scale particles, we have started with polystyrene particles of diameter D=1 μm, whose results are shown in FIG. 9. These particles can be reliably manipulated at speeds as large as 0.2 mm/s in our system, without tweaking or optimizing the trapping beam. Theoretically, the maximum manipulation speed, $V_{max}$, is governed by the force balance between the optical trap and the Stokes' drag force of the particle moving through the liquid. This balance implies $$v_{max} = \frac{F_{grad,max}}{3\pi\mu D}, \tag{3}$$

where $F_{grad,max}$ is the maximum gradient force exerted by the optical trap, and μ is the viscosity of the surrounding medium (water). We believe that the current maximum manipulation speed of 0.2 mm/s for 1 m polystyrene spheres can be significantly improved. Combining Eqs. (1) and (3), $F_{grad}$ is proportional to laser beam power, and thus $v_{max}$ is proportional to laser beam power. This expected linear relationship is in contrast to that shown in FIG. 9, where a nonlinear dependence is observed, which may be due to hydrodynamic effects from the nearby walls of the chamber, or may be due to vibrations in the translation stage that scale with speed. In these tests, we have currently only used 3% of the maximum power of the laser beam. We expect further improvements to the maximum manipulation speed through modifying the filling fraction of the objective, adjusting the polarization state of the laser beam, and through fine tuning the correction collar and divergence of the incoming laser beam.

We expect to be able to trap gold nanoparticles with diameters as small as 18 nm. A general rule of thumb is that a stable trap requires a potential well depth of $W<-10$ kT, where k is Boltzmann's constant, and T is the temperature. The potential well depth can be calculated using Eq. (1), and the equation, $$W = -\int_{-\infty}^{0} F_{grad} \cdot \hat{x} dx \propto \text{Re}\{\alpha\}, \quad (4)$$

We would thus expect to be able to trap any type of particle with $\text{Re}\{\alpha\}$ greater than that of the 18 nm gold particle. From Eq. (2), this would correspond to polystyrene particles as small as 39 nm, and silica particles as small as 49 nm. These values are based on the same trapping power as used in Hansen et al., Expanding the optical trapping range of gold nanoparticles. Nano Lett. 5, 1937-1942 (2005); however, since we can use higher laser power, we expect to be able to trap even smaller particles.

The strength of the trap also affects the accuracy with which particles can be positioned, or in other words the ability of the trap to oppose Brownian motion, as derived below. If we assume the profile of our focused beam is Gaussian, then its complex electric field is $$E(r) = \text{Re}\left\{E_0 e^{-\frac{r^2}{w^2}} e^{-i\omega t}\right\} \quad (5)$$

where w=FWHM/$\sqrt{4\ln 2}$ defines the spot size in terms of the beam's full width at half-maximum (FWHM), ω is the frequency of the light, and t is time. The optical trap is analogous to a spring-mass system with an effective spring constant $$K = -\frac{\partial F}{\partial r}\bigg|_{r=0}. \quad (6)$$

Combining Eqs. (1), (5), and (6), the resulting spring constant is, $K=\text{Re}\{\alpha\}E_0^2/w^2$. The positional accuracy of the trap is governed by the expected value of the radial position of the bead due to thermal forces, calculated using Boltzmann statistics $$\langle r \rangle = \sqrt{\frac{\pi kT}{2K}}. \quad (7)$$

Let us assume that we have an optical trap with a spot size FWHM=λ/2=532 nm that can trap an 18 nm gold nanoparticle with 10 kT potential well depth. This combination of parameters represents the worst case in terms of positional accuracy. The potential well depth, in concert with Eqs. (4) and (5), can be used to infer a value of $E_0$, which in turn provides a value of $\langle r \rangle$=60 nm. While this positional accuracy would likely make the technique infeasible for particles this small, it turns out that $\langle r \rangle \propto D^{-3/2}$, and therefore larger particles exhibit acceptable positional accuracies of $\langle r \rangle$=13 nm for a 50 nm diameter gold particle, and $\langle r \rangle$=5 nm for a 100 nm gold particle. These values of $\langle r \rangle$ provide more than sufficient accuracy to optimally locate nanoparticles in the evanescent zone of the microtoroid. It should also be emphasized that our platform has a stronger laser than that used in Hansen, id., and thus we expect even better positional accuracies than the values quoted here. While external disturbances, vibrations, etc. can also impact positional accuracy, these effects can be mitigated using vibration-isolated optical tables and other engineering control measures.

Figure 10:
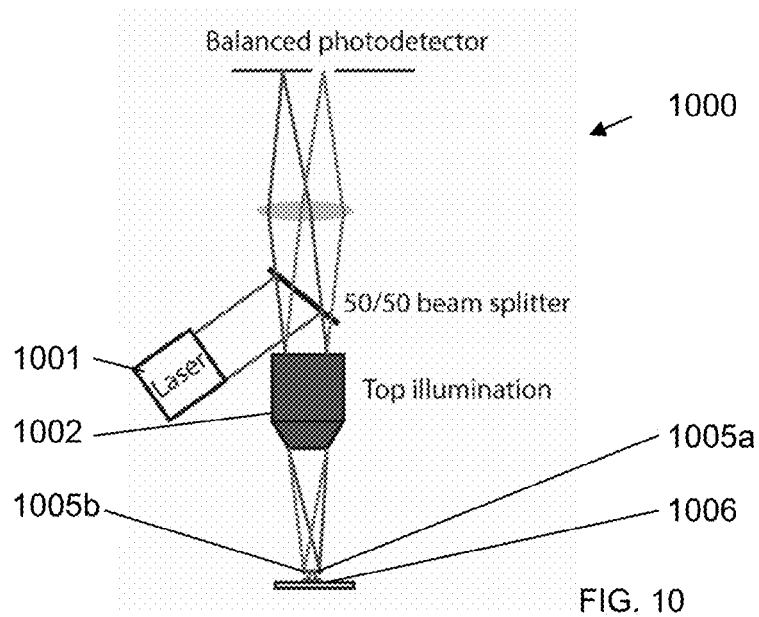
FIG. 10 schematically illustrates a nanomanufactured toroid performance testing apparatus, according to an illustrative embodiment of the invention.

FIG. 10 schematically illustrates a nanomanufactured toroid performance testing apparatus 1000, according to an illustrative embodiment of the invention. A tunable laser 1001 is focused using a standard microscope objective 1002 onto a specific nanostructure 1005a on the rim of the microtoroid 1006 to generate a whispering gallery mode inside the toroid. Readout is performed by imaging a nanostructure 1005b that is diametrically opposed to the in-coupling nanostructure onto the active area of a balanced photodetector 1010. The rest of the testing apparatus is the same as that depicted in the block diagram in FIG. 4.

In order to fix the gold nanoparticles in precise positions on the microtoroid's rim, we covalently bind a silane-PEG-biotin linker to the surface. The gold nanoparticle is coated with streptavidin, which allows for strong binding to the biotin linker. The streptavidin coating on the nanoparticles will also be helpful in functionalizing these nanoparticles to specifically capture target analyte molecules for sensing. We will confirm the presence and location of the gold nanoparticles using scanning electron microscopy (SEM).

Other than biotin-avidin interactions, there are many other binding mechanisms that may be used. These include antigen-antibody interactions, the binding of complimentary DNA oligomers, as well as physical interactions such as electrostatic, Van der Waals, steric, and covalent bonding. These types of interactions may be used to bind nanoparticles to the surface of the toroid, as well as to bind one or more linkers to the nanoparticle(s) and/or toroid to facilitate their linkage.

Figure 12:
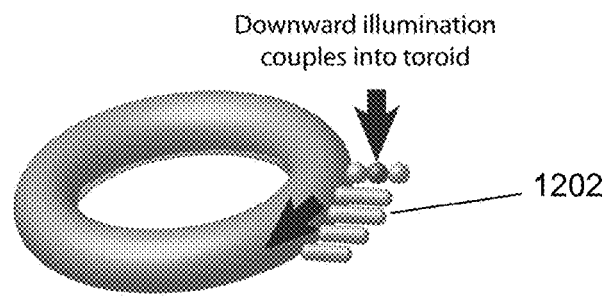
FIG. 12: Schematic illustration of a phased array (or metasurface) that has been attached to the surface of the microtoroid, according to an illustrative embodiment of the invention.

In addition to using single nanoparticles to couple light into and out of the optical resonator, we also propose to use phased arrays of nanoparticles 1202 as illustrated in FIG. 12. These phased arrays can be used to provide more directional and enhanced coupling both into and out-of the optical resonator. These arrays can function similarly to, for example, Yagi-Uda antennas, which are widely adopted for the receipt of broadcast television signals. Beyond improving coupling efficiency, such antenna-like arrays can also directly aid in analyte sensing. FIG. 12 schematically illustrates a phased array (or metasurface) that has been attached to the surface of the microtoroid. The phased array consists of nanoparticles whose sizes, shapes, compositions, orientations, and positions have been carefully chosen to couple light into the toroid. Similar principles can be used to couple light out of the toroid, or fabricate signal-enhancing nanostructures.

It is also possible to use complex assemblies of particles that function as a single entity, similar to a nanophotonic device based on the concept of photonic metamaterials. This device can be optimized to transduce far-field radiation with electromagnetic near-fields. A phased array can be considered as one such type of complex particle assembly, although highly compact nanoparticle arrays are likely better considered in terms of a metamaterial conceptual framework instead of a phased-array conceptual framework (FIG. 12).

We will test the performance of the coupled resonator in two phases: first without any target analyte, and second, in the presence of target analytes. These two phases will allow us to separately understand the physical properties and the chemical properties of the nanomanufactured device. In the first phase, we will evaluate the performance of the device by experimentally measuring its Q-factor and comparing it to simulations. Our experimental approach to measuring Q-factor is depicted in FIG. 13. We will couple light into the device by positioning one of the attached gold nanoparticles at the focus of a microscope objective (NA>0.5), and sending collimated laser light into the objective, so that it focuses on the nanoparticle. This focused light will excite plasmonic oscillations of the nanoparticle. These plasmonic oscillations will evanescently couple into the microtoroid optical resonator, generating a circulating mode of light within the resonator. This circulating mode will be strongly amplified when the frequency of the incident laser light matches the resonant frequency of the microtoroid-nanospheres system of coupled oscillators.

The degree of amplification will be tracked by imaging the scattering from another nanostructure. This scattered light will be collected out of our device with the same objective with a beamsplitter 223 placed behind the objective to direct the light to an auto-balanced photo-receiver 209 (FIG. 12). Because the in-coupling nanoparticle 205a is significantly separated in space from the out-coupling nanoparticle 205b, it is possible to spatially resolve these two points in the image-space of the objective and make sure that simple back-scattering from the in-coupling nanoparticle is not collected by the auto-balanced photo-receiver. The degree of amplification as a function of the wavelength of the tunable laser source will be used to measure the linewidth of the resonances of the coupled microtoroid-nanostructure system. Measuring these linewidths is equivalent to measuring the Q-factor of the system.

We will also quantify the frequency shifts that occur when target analytes bind to the device, as well as quantifying the signal-to-noise with which we can measure these shifts. Target molecules will be captured using biotinylated antibodies, which will have been previously bound to the streptavidin-coated gold nanoparticles. The shift in resonance will be detected by monitoring the same out-coupling nanoparticle that was previously used to measure the device Q-factor.

To further miniaturize this device, we will replace the microscope objective with a small lens to make the system more compact and cost-effective. For this application, it is not necessary to have a super-high numerical aperture lens (spot sizes of ~10 μm would be sufficient), and aberrations can be tolerated. Eliminating the optical fiber reduces the precision with which the toroid needs to be positioned relative to the optical delivery system (now far-field lenses), and thereby the major roadblock in the path toward mass-producible and portable sensors based on this technology. By moving to lower quality coupling optics, it is likely that there may be some decrease in SNR, which we will measure experimentally.

The first analyte we will test are 20 nm diameter biotin-coated polystyrene beads, which are expected to bind to the surface of streptavidin-coated gold nanospheres that we previously adhered to the surface of the toroid in our nanomanufacturing step. We will measure the change in resonance frequency, and compare the observed value to that observed when polystyrene beads bind directly to a portion of the toroid without a nanoshell (these latter results are from our previously-published data. The change in resonance frequency will be monitored over time using the output of the photodiode. For a particle binding to a bare resonator, the shift upon binding of a particle is given by:

$$d = 2a = 2\left(\frac{2V_m E_{0,max}^2}{DE_0^2(r_s)}\right)^{1/3}\left(\frac{\Delta\lambda}{\lambda}\right)^{1/3}, \qquad (8)$$

where d is the diameter of a bound particle, α is the radius, $V_m$ is the electromagnetic mode volume of the microtoroid, D is a dielectric factor calculated from the index of refraction of the bound particle and the background solution, $E_{0,max}^2$ is the electric field intensity at the microtoroid equator, and $E_0^2(r_s)$ is the intensity of the electric field at the microtoroid surface. $V_m$ and $E_{0,max}^2/E_0^2(r_s)$ are determined from finite element simulations.

We will proceed to test progressively smaller analytes to determine the minimum particle/molecule size that can be detected by this coupled system. It is expected that the minimum particle size will be significantly smaller than for the bare toroid. For each particle size, we will quantify the SNR of the detection process.

Once we demonstrate successfully coupling light into and out of our device using nanospheres, we will progress to positioning a more complicated nanobowtie structure on the rim of a microtoroid. FIG. 11 is an artistic rendering of a gold nanobowtie 505a (not to scale) bound to the surface of a microtoroid. Gold nanobowties have been shown to have a 1000× electric field enhancement at the center of the bowtie. This electric field enhancement will cause in corresponding increase in the signal to noise ratio of the device. We will manufacture gold bowties by using commercially available gold nanotriangles ~50 nm in height, and independently position them so that their relative spacing is 10-20 nanometers apart based on the precision of the optical tweezers around the rim of the microtoroid. 50 nm is chosen as it should be able to be easily trapped via optical tweezers. The spacing between the triangles will be made as small as possible, within the placement precision of the optical tweezers, which we estimate to be ~10 nm. To determine how many gold nanotriangles we will need and how far apart they should be spaced (pitch) we will first perform electromagnetic simulations, again using COMSOL and MEEP.

We will fix the nanobowties to the surface of the microtoroid using strepavidin-biotin coupling. In this procedure we will functionalize the toroid surface using a silane-PEG-biotin molecule. The gold nanotriangles will be functionalized with thiol-PEG-biotin molecules, and subsequently coated with free streptavidin molecules. These streptavidin molecules coating the gold triangles will then spontaneously bind to the biotinylated microtoroid surface. We will hold the gold triangles with our optical tweezers until they firmly adhere to the surface. The presence of the nanobowties will be confirmed via SEM, and the gap spacing will be measured, which is a critical parameter in the degree of plasmonic enhancement that these structures can supply.

In addition to our numerical simulations using COMSOL and MEEP, we will experimentally measure the signal enhancement provided by the nanobowties by binding a 20 nm polystyrene bead to the center of the bowtie and comparing this to the previous signal shift observed from 20 nm polystyrene beads binding to a bare resonator, as well as by testing smaller molecules.

The metal nanostructures may be used, with particular advantage, for (1) optimized sensing hotspots and (2) as a means to couple light into and out of the optical resonators without the need for an external waveguide, as is known in the art. The embodied devices may advantageously be applicable as extremely sensitive and portable biological and chemical sensors, as well as in silicon photonics for computing and communications. In communications, optical resonators can be used for wavelength division multiplexing and switching/routing of optical signals. The embodied invention provides a new way of coupling to these resonators in these applications. Other non-limiting applications include second harmonic generation and surface enhanced Raman scattering, which both benefit from an enhanced interaction of light with matter. In these applications, the combination of a nanoparticle with an optical microresonator leads to a hot-spot in the electric field intensity that can greatly enhance second harmonic generation and surface-enhanced Raman scattering because these processes scale nonlinearly (exponent>1) with electric field intensity.

We claim:

1. An optical apparatus for detecting at least one molecule in a sample, comprising:
   a whispering gallery mode optical resonator comprising a curved resonance portion, wherein said curved resonance portion has an outermost rim; and
   a first nanoparticle attached at a position on said outermost rim of said curved resonance portion of said whispering gallery mode optical resonator,
   wherein said first nanoparticle has a structure and composition to facilitate coupling light at least one of into or out of said curved resonance portion of said whispering gallery mode optical resonator,
   and
   wherein said first nanoparticle further creates a detection enhancement structure for enhanced detection of said at least one molecule of said sample when attached to said first nanoparticle.

2. The optical apparatus of claim 1, wherein the first nanoparticle is non-spherical.

3. The optical apparatus of claim 2, wherein the non-spherical nanoparticle has an orientation that is aligned with a polarization of light propagating in the whispering gallery mode optical resonator.

4. The optical apparatus of claim 2, wherein the non-spherical nanoparticle has a bow-tie geometry.

5. The optical apparatus of claim 1, wherein the first nanoparticle is chemically attached to the microtoroid.

6. The optical apparatus of claim 1, further comprising a plurality of nanoparticles attached at respective positions on said outermost rim of said curved resonance portion of said whispering gallery mode optical resonator, wherein the first nanoparticle and the plurality of nanoparticles comprise a phased array of nanoparticles.

7. The optical apparatus of claim 1, further comprising a plurality of nanoparticles attached at respective positions on said outermost rim of said curved resonance portion of said whispering gallery mode optical resonator, wherein the first nanoparticle and the plurality of nanoparticles comprise one or more groupings of nanoparticles.

8. The optical apparatus of claim 1, further comprising a plurality of nanoparticles attached at respective positions on said outermost rim of said curved resonance portion of said whispering gallery mode optical resonator, wherein said first nanoparticle and said plurality of nanoparticles form assemblies of nanoparticles.

9. The optical apparatus of claim 1, wherein the whispering gallery mode optical resonator is characterized by a quality factor, Q, that is equal to or greater than $10^5$.

10. The optical apparatus according to claim 1, further comprising a second nanoparticle attached at a second position on said outermost rim of said curved resonance portion of said whispering gallery mode optical resonator,
    wherein said second nanoparticle has a structure and composition to facilitate coupling light at least one of into or out of said curved resonance portion of said whispering gallery mode optical resonator,
    wherein said second nanoparticle further creates a second detection enhancement structure for enhanced detection of said at least one molecule of said sample when attached to said second nanoparticle, and
    wherein said whispering gallery mode optical resonator is characterized by a quality factor, Q, that is equal to or greater than $10^5$.

11. The optical apparatus of claim 10, wherein said first and second nanoparticles are disposed diametrically opposed on an equatorial region of said whispering gallery mode optical resonator, and wherein said whispering gallery mode optical resonator is a microtoroid whispering gallery mode optical resonator.

12. The optical apparatus according to claim 10, further comprising:
    an optical source arranged to illuminate at least one of said first and second nanoparticles to provide enhanced optical coupling into said whispering gallery mode optical resonator; and
    an optical detector arranged to receive light coupled out of said whispering gallery mode optical resonator by at least one of said first and second nanoparticles to provide enhanced outcoupling,
    wherein said optical detector is further configured to distinguish light coupled out of said whispering gallery mode optical resonator from illumination light that is at least one of scattered from or reflected from said whispering gallery mode optical resonator or said first or second nanoparticles.

* * * * *